United States Patent [19]
Yamada

[11] Patent Number: 5,437,836
[45] Date of Patent: Aug. 1, 1995

[54] METHOD OF AND CONTAINER FOR TREATING WASTE LIQUID CONTAINING BODY FLUID

[75] Inventor: Keiichi Yamada, Sakai, Japan

[73] Assignee: Daiken Iki Co., Ltd., Japan

[21] Appl. No.: 167,821

[22] PCT Filed: Apr. 2, 1993

[86] PCT No.: PCT/JP93/00437

§ 371 Date: Dec. 17, 1993

§ 102(e) Date: Dec. 17, 1993

[87] PCT Pub. No.: WO93/20855

PCT Pub. Date: Oct. 28, 1993

[30] Foreign Application Priority Data

Apr. 17, 1992 [JP] Japan .................................. 4-098151

[51] Int. Cl.6 ...................... B01D 63/02; C02F 9/00; A61M 1/00
[52] U.S. Cl. ..................... 422/1; 210/257.2; 604/317; 604/319
[58] Field of Search ............... 210/500.23, 321.78, 210/321.88, 257.2; 604/317, 319, 320, 322–324, 405, 406; 422/1

[56] References Cited

U.S. PATENT DOCUMENTS

| | | |
|---|---|---|
| 3,685,517 | 8/1972 | Reynolds et al. . |
| 4,276,170 | 6/1981 | Vaillancourt ......................... 210/436 |
| 4,402,687 | 9/1983 | Denty et al. ......................... 604/319 |
| 4,516,973 | 5/1985 | Telang ................................. 604/319 |
| 4,573,983 | 3/1986 | Annis ................................... 604/322 |
| 5,049,273 | 9/1991 | Knox ................................ 604/319 X |
| 5,130,015 | 7/1992 | Simizu et al. ........................ 210/136 |

FOREIGN PATENT DOCUMENTS 487679 3/1992 Japan .

*Primary Examiner*—Robert J. Warden
*Assistant Examiner*—E. Leigh Dawson
*Attorney, Agent, or Firm*—Sixbey, Friedman, Leedom & Ferguson; David S. Safran

[57] ABSTRACT

The present invention relates to the treatment for waste liquid containing a body fluid such as blood and lymph, and provides a method for treating a waste liquid containing a body fluid, which makes easy the transport of the container after collection of a waste liquid, the incineration of the container, and the sterilization of the water content in the waste liquid if necessary, and all; and a treating container suitable for carrying out the method.

19 Claims, 4 Drawing Sheets

5,437,836

METHOD OF AND CONTAINER FOR TREATING WASTE LIQUID CONTAINING BODY FLUID

TECHNICAL FIELD

The present-invention relates to methods of and containers for treating a body fluid such as blood and lymph generated during medical treatment or surgery for injury and disease, a physiological saline solution after washing the operated part and the oral cavity, and a waste liquid containing a body fluid such as urine and stool.

BACKGROUND ART

A waste liquid containing a body fluid released from a patient during surgery and medical treatment (hereinafter, the wording "waste liquid" means the infectious liquid containing a body fluid ) is aspirated and collected in a collecting bottle with an applied negative pressure. After that, the waste liquid is flushed down the drain. For this purpose, a glass bottle (the capacity of which is in the range of 5 to 8 liters) is used. This bottle is, however, heavy, and is cumbersome in discarding the hazardous waste liquid. Moreover, from a point of view of environmental protection, medical waste should be sterilized before being returned to environment. Under process of autoclave sterilization, the waste liquid containing the body fluid emits an offensive smell. Germicidal agent becomes ineffective in the presence of highly concentrated organic mater such as blood cells and fat. Thus, in recent years, the trend is toward in use of one use only container made of synthetic resin. The one use only container can be incinerated together with the waste liquid.

As the disposal container, U.S. Pat. No. 3,685,517 discloses such a treating container 55 as shown in FIG. 6, wherein a synthetic resin made bag member 54 is welded to a firm synthetic resin made cover 53 with an outlet 51 and an inlet 52. This container 55 is used in such a manner that the bag member 54 is inserted in a firm pressure reducing vessel 56 and the upper cover 53 is air-tightly fitted to the opening of the pressure reducing vessel 56. The upper cover 53 has a first through-hole 57 and a second through-hole 58. The first through-hole 57 communicates with the space between the inner surface of the pressure reducing vessel 56 and the outer surface of the bag member 54, whereas the second through-hole 58 communicates with a conduit 59 projectingly provided in the bag member 54. When the outlet 51 is connected to a pressure reducing source, the bag member 54 is swelled in the pressure reducing vessel and concurrently the waste liquid is aspirated through the inlet 52.

Using the one use only container eliminates the troublesome works such as a work for discarding the waste liquid and a work for washing the interior of the bottle after discarding the waste liquid. The prior art container, however, has the following disadvantage: namely, although the container itself is extremely reduced in its weight by changing the material thereof from glass to synthetic, the container filled with the waste liquid is still heavy because the content therein is mainly composed of water. This takes a lot of labor in its transport and requires a large amount of energy in its incineration.

In view of the above situation, the present invention has been made. Accordingly, an object of the present invention is to provide a method for treating a waste liquid containing a body fluid, which makes easy the transport of the container and subsequent incineration: and a container suitable for carrying out the method.

DISCLOSURE OF THE INVENTION

A method of the present invention comprises the steps of: sucking and collecting a waste liquid containing a body fluid such as a body fluid or a washing liquid for the body cavity in a synthetic resin made storage container; removing the water content in the waste liquid through a filter to separate infectious microbes; and discarding the storage container containing the infectious microbes in the waste liquid together with the filter.

The treating container of the present invention suitable for carrying out the method mentioned above is composed of a synthetic resin made storage container and a cover with an inlet and an outlet. The storage container is further equipped with a filter to separate infectious microbes and a discharge tube for discharging the water content in the waste liquid passing through the filter, the discharge tube being provided with an opening/closing valve. Preferably, the filter is constituted of a secondary filter capable of separating the infectious microbes and a primary filter for preventing the blocking of the secondary filter. Further, the filter is preferably provided at such a position as to project from the inner surface of the storage container toward the inside thereof. The storage container is preferably capable of expansion and contraction.

According to the present invention, the waste liquid after being sucked and collected in the storage container is treated such that the water content therein is discharged from the discharge tube to the outside through the filter by opening of the opening/closing valve. The filter is able to separate the infectious microbes, and hence to enclose bacteria and the like harmful to a human body in the storage container together with organic matter such as fat, blood corpuscles and the like. In this case, by pressurizing the waste liquid in the treating container and sucking the flow-out side of the discharge tube, it is possible to increase the filtration rate. In addition, since the filter is constituted of the secondary filter capable of separating the infectious microbes and the primary filter separating bigger particulates and preventing the blocking of the secondary filter, it is possible to increase the filtration efficiency. Further, by providing the filter at such a position as to project from the inner surface of the storage container toward the inside thereof, it is possible to prevent solid components which, has high specific gravity in the body fluid such as blood clot from adhering on the surface of the filter membrane in a covering manner. The storage container after the water content in the waste liquid is removed is made light, and is easily incinerated. Even if the filter cannot separate the smallest infectious microbes such as viruses from the water content, the water content can easily be sterilized by adding germicidal agent or applying heat, because almost all organic matter and fat have been removed from the water content. In this case, the storage container is incinerated together with the filter, which eliminates the hazard of leaking the infectious microbes to the outside. By making the storage container expandable and contractible, it is possible to make smaller the capacity of the treating container before and after the usage, which is convenient for the storage and transport thereof.

Namely, according to the present invention, the waste liquid containing the body fluid is sucked and collected in the treating container, and then filtered by the filter provided in the treating container for discharging the water content in the waste liquid to the outside, it is possible to make light the treating container, and to make easy its incineration, and to make easy sterilization of the water content if necessary. In addition, the filter is constituted of the primary filter and the secondary filter. The primary filter makes it possible to prevent the secondary filter with a micro pores from being clogged quickly, and hence to prevent the lowering of the filtration efficiency.

BEST MODE OF CARRYING OUT THE INVENTION

Figure 1:
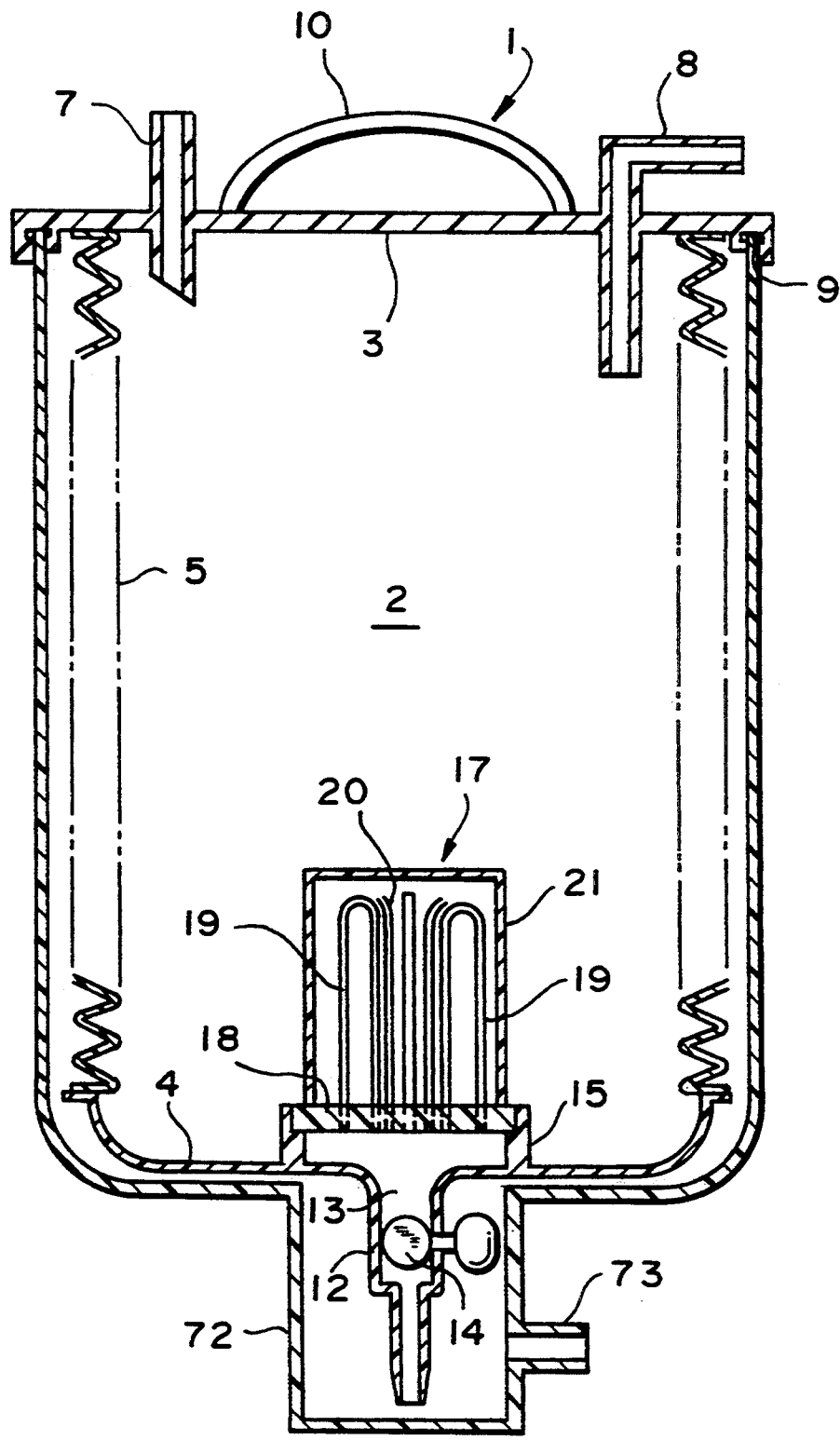
FIG. 1 is a sectional view of a treating container according to an embodiment which is accommodated in a pressure reducing vessel.

FIG. 1 shows a treating container 1 and its auxiliary equipment according to an embodiment. The treating container 1 includes a vertically expandable storage container 2. The storage container 2 is constituted of an upper cover 3, a lower cover 4, and a cylindrical side wall portion 5 for connecting both the covers 3 and 4. The side wall portion 5 has a vertically expandable and contractible bellows-like structure, or is made by folding of a flexible synthetic resin sheet. The upper cover 3 and the lower cover 4 are made of relatively firm synthetic resin. The upper end of the side wall portion 5 is fixed on the lower surface of the upper cover 3 while the lower end of the side wall portion 5 is fixed on the peripheral edge of the lower cover 4, each being fixed by welding or adhering. The above synthetic resin comprises a thermoplastic resin having a good formability and a transparent or semitransparent property such as polyvinylchloride, polypropylene and polyethylene. In addition, the side wall portion 5 and the lower cover 4 of the storage container 2 are accommodated in a firm pressure reducing vessel 71 in collection of a waste liquid.

The upper cover 3 is formed integrally with an outlet 8 and an inlet 7 which are communicated with the interior of the treating container. On the lower portion of the peripheral edge of the upper cover 3, a recessed groove 9 is provided to be air-tightly snap-fitted around the peripheral edge of the upper edge of the pressure reducing vessel 71. A handle 10, which is used in taking out the treating container 1 from the pressure reducing vessel 71 and in transporting the container, is formed on the upper surface of the upper cover 3. The pressure reducing vessel 71 mentioned above is repeatedly used, and which is formed of a transparent or semitransparent glass or synthetic resin.

A discharge tube 12 is formed at the center of the lower cover 4. An opening/closing valve 14 is mounted in an upper conduit 13 of the discharge tube 12. A short cylindrical supporting member 15 is formed on the upper portion of the lower cover 4 so as to project to the inside and to surround the opening of the discharge tube 12. A filter unit 17 is liquid-tightly fixed on the supporting member 15 by welding or adhering. A bottom portion of the pressure reducing vessel 71 has a cylindrical portion 72, cylindrical portion 72 projecting therefrom to accommodate the discharge tube 12 and an outlet 73.

The filter unit 17 is constituted of a base plate 18 fixed on the upper edge of the supporting member 15, a secondary filter 20 composed of a group of hollow fibrous membrane 19 planted on the base plate 18 in a reversed U-shape, and a primary filter 21 for preventing the blocking of the secondary filter 20. The primary filter 21 is fixed on the peripheral edge of the upper portion of the base plate 18 so as to surround the secondary filter 20.

Figure 2:
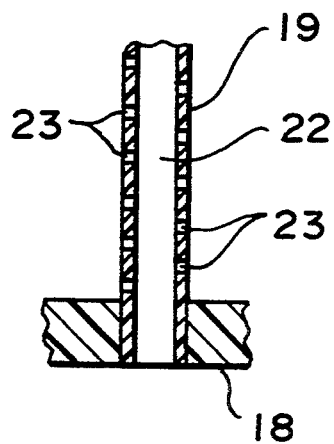
FIG. 2 is a partially sectional view of the vicinity of a base plate of a hollow fibrous membrane constituting a secondary filter.

FIG. 2 is an example of an enlarged view of the each hollow fibrous membrane 19 constituting the secondary filter 20. The membrane 19 has many micro-openings (pores) 23 communicated with the hollow portion 22, and is fixed at its end on the base plate 18. The membrane 19 is suitable for this embodiment because the total filtration area of the filter can easily be enlarged by simply increasing the number of the fibers. Preferably, samples of materials for the membrane 19 include known hydrophobic synthetic resins such as polyethylene, polypropylene, polysulfone, polyamide and the like, which are subjected to hydrophilic treatment; or hydrophilic synthetic resin.

The pore size of the membrane 19 must be made small enough to separate infectious microbes. The typical size of the infectious microbes such as bacteria and blood cells is bigger than 1 $\mu$m in size, and accordingly, the pore size should be in the range of from 0.5 to 0.1 $\mu$m. The smallest infectious microbes, viruses are usually 0.02 to 0.4 $\mu$m in size or even smaller, thus the pore size of about 0.01 $\mu$m is required for directly separating the viruses. However, the viruses require other organic cells such as microbes or blood cells as the parasitic hosts for their survival, and these particulates are bigger than 1 $\mu$m in size. Moreover, the waste liquid containing only the small infectious microbes such as viruses can easily be sterilized by autoclave sterilization or germicidal agent sterilization, because most organic matter have been removed from the waste liquid. Therefore, the secondary filter 20 capable of separating bacteria is sufficient for practical purposes. The total filtration area required of the secondary filter 20 is dependent on the total capacity of the stored waste liquid in the treating container 1; for example, it should be approximately 0.5 $m^2$ for 5 liter of the waste liquid. In addition, as for the hollow fibrous membrane 19 planted on the base plate 18, many types are commercially available, for example, STERAPORE by Mitsubishi Rayon Co., Ltd.

Figure 3:
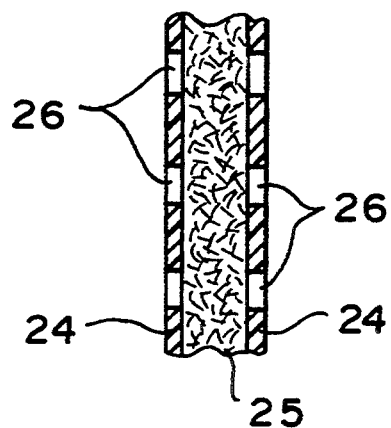
FIG. 3 is a partially sectional view showing the structure of a primary filter.

On the other hand, as shown in FIG. 3, the primary filter 21 has such a structure that a sheet-filter 25 such as a paper filter or a non-woven fabric filter is sandwiched between two plates 24, 24. The pressing plate 24 has many through-holes 26, each of which has a diameter of about several mm. The pore size of the primary filter 21, should be about 10 μm or bigger. The primary filter can prevent relatively larger particulates such as high protein, fat from blocking of the secondary filter 20.

For collecting a waste liquid by using the above-mentioned treating container1, first, in such a state as to close the opening/closing valve 14 of the discharge tube 12, the portion of the treating container 1 is inserted in the pressure reducing vessel 71, and the upper cover 3 is air-tightly fitted around the upper edge of the pressure reducing vessel 71. The outlet 8 for the upper cover 3 and the opening 73 of the pressure reducing vessel 71 are connected to a pressure reducing source such as a vacuum pump, and a suction tube is connected to the inlet 7. The value of the gauge pressure of the pressure reducing source is generally about −400 mmHg. Since the suction tube communicates with the atmosphere, the value of the pressure in the treating container 1 is slightly larger than that of the space between the pressure reducing vessel 71, and the treating container 1. Consequently, the side wall portion 5 of the treating container 1 is expanded to be swelled largely.

Figure 4:
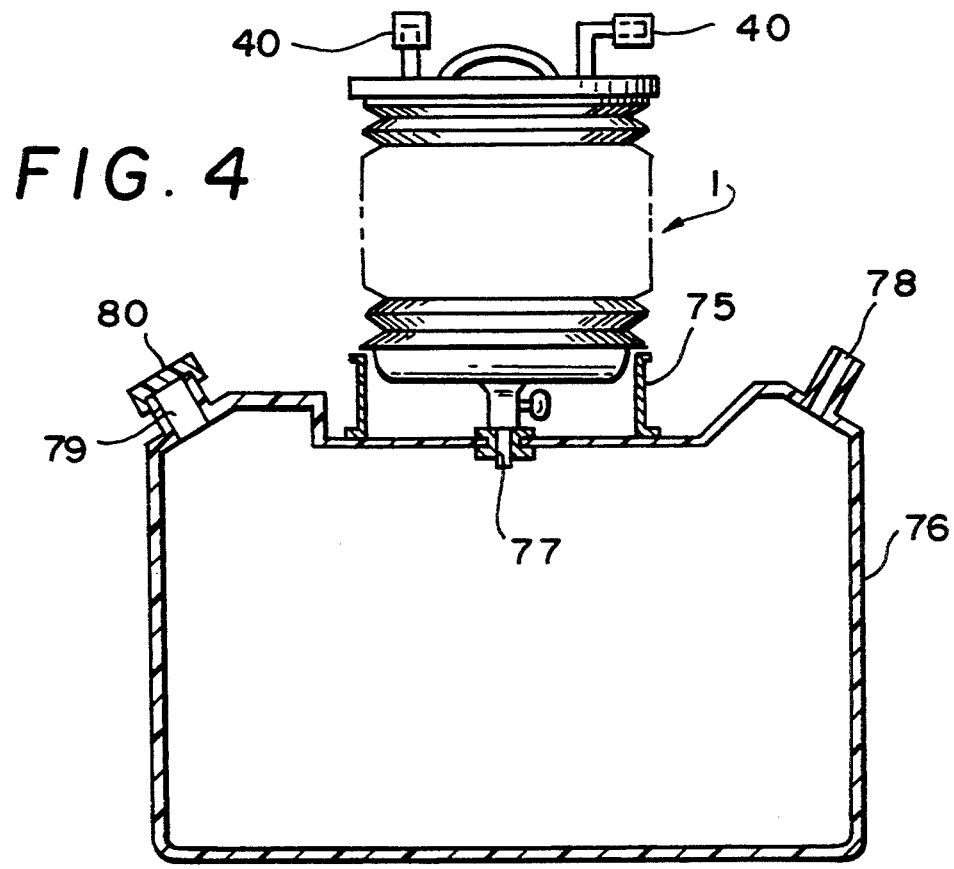
FIG. 4 is a partially sectional view showing a filtering state of the treating container according to the embodiment.

After completion of the collection of the waste liquid, the connection tubes connected to the suction tube and the pressure reducing tube are removed from the inlet 7 and the outlet 8 respectively and caps 40 (see FIG. 4) are mounted on the outlet 8 and the inlet 7. By holding the handle 10, the treating container 1 is pulled out of the pressure reducing vessel 71, and is mounted on a tank 76 through a supporting base 75 as shown in FIG. 4. At this time, the leading edge of the discharge tube 12 is inserted in an insertion port 77 of the tank 76. Subsequently, by opening the opening/closing valve 14, the waste liquid in the treating container 1 is filtered by the filter unit 17, and the water content, in which most organic matter have been eliminated, is allowed to flow in the tank 76. At this time, in order to increase the filtration rate, the treating container 1 may be pressed in the direction of contracting the bellows of the side wall portion 5, or a suction port 78 provided on the tank 76 may be connected to the pressure reducing source. Further, the pressurized air may be fed in the treating container 1 through the outlet 8 of the treating container 1. When the filtration is completed, the treating container 1 is removed from the tank 76 after the opening/closing valve 14 is closed. The content left inside the treating container 1 is mainly composed of solid components such as organic matters and cells, so that the treating container 1 is made light to be transported and is easily incinerated by using an incinerator with a relatively small amount of energy. Finally, sterilization of the liquid drained in the tank 76 may be done by adding germicidal agent or applying heat to the liquid. In addition, reference numeral 79 indicates a drain port of the tank 76, and is fitted with a cap 80.

Figure 5:
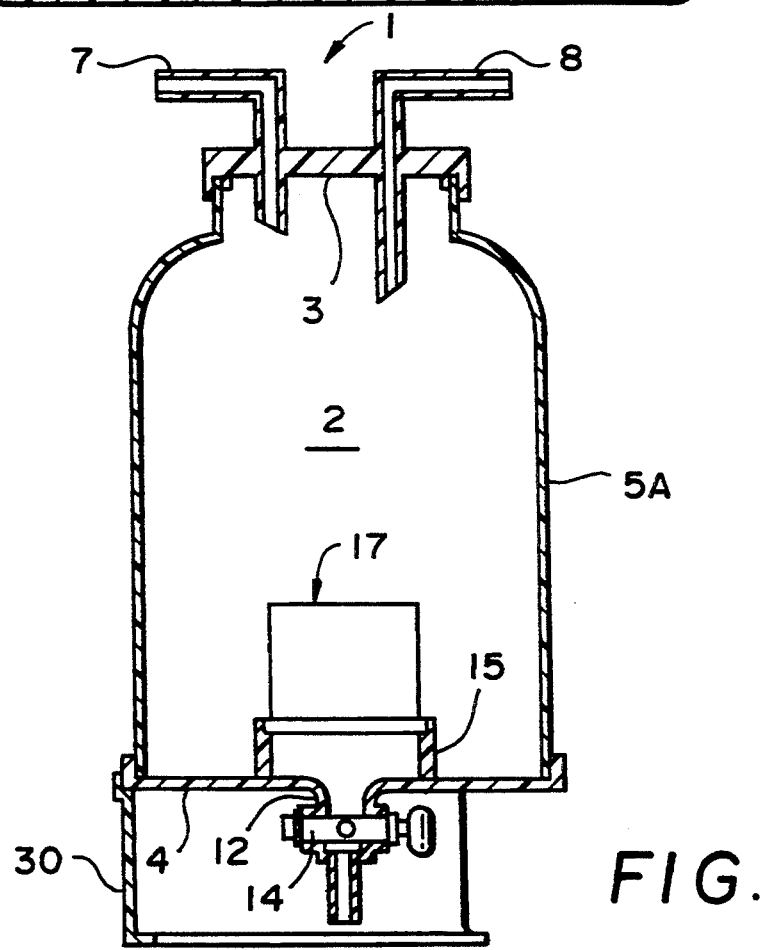
FIG. 5 is a sectional view of a treating container according to another embodiment.
Figure 6:
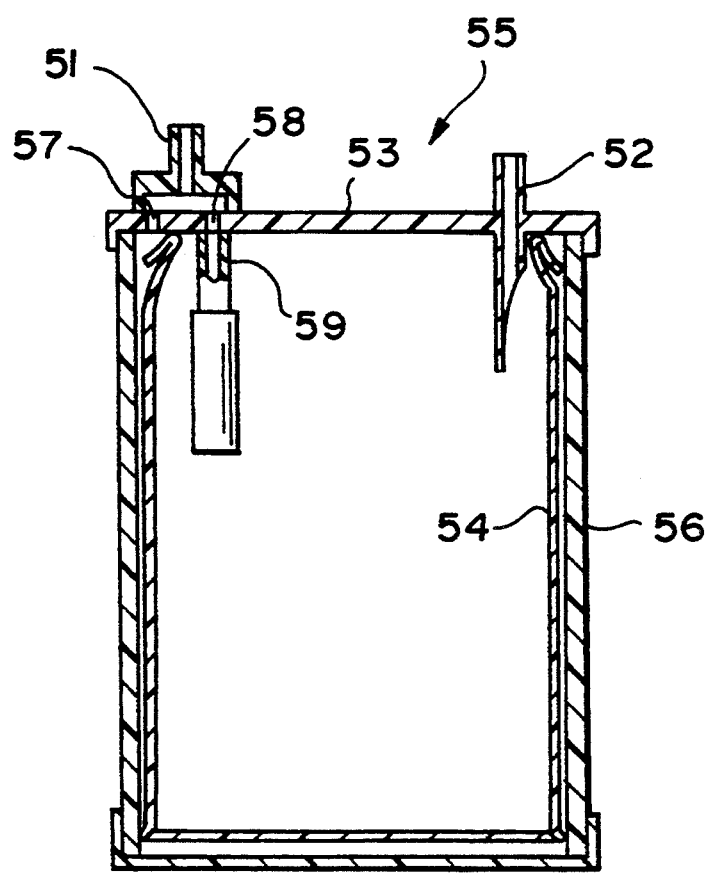
FIG. 6 is a sectional view of a conventional treating container accommodated in a pressure reducing vessel.

According to the embodiment mentioned above, the treating container 1 has the side wall portion 5 of the storage container 2 which is made to be of a bellows-like structure or made by folding of a flexible sheet. However, as shown in FIG. 5, the side wall portion 5A may be formed of a cylindrical body. In addition, reference numeral 30 indicates a supporting base for preventing the breakage of the discharge tube 12, wherein the upper edge thereof is snap-fitted around the outer peripheral edge of the lower cover 4, and part of the side wall is cut-out for making easy the operation of the opening/closing valve 14.

In the embodiment as shown in FIG. 1, hollow fibrous membrane 19 is used as the secondary filter 20 of the filter unit 17; however, other types of filters are of course used. The primary filter 21 does not necessarily have a laminated structure as in this embodiment; for example, it may be a type in which a non-woven fabric filter is formed in a cap shape. Further, the exhaust tube 73 is not necessarily provided on the lower portion of the pressure reducing vessel 71, and the space between the inner surface of the pressure reducing vessel 71 and the side wall portion 5 of the treating container 1 or the outer surface of the lower cover 4 may be in the pressure-reducing state by some means; for example, as in the prior art, a passage communicated between the outlet 8 and the above space may be provided on the upper cover 3.

INDUSTRIAL APPLICABILITY

The present invention is excellent in handling and safety, and further useful as a method of and a container for treating infectious liquid such as blood and lymph generated during medical treatment or surgery for injury and disease, a physiological saline solution after washing the operated part and the inside of the body, and infectious liquid containing a body fluid such as urine and stool.

I claim:
1. A method of treating a waste liquid containing a body fluid comprising the steps of:
   sucking and collecting a waste liquid containing a body fluid in a storage container made of synthetic resin;
   removing a water content in said waste liquid from said storage container through a microporous filter disposed between an interior since of the container and an inlet end of a discharge tube of the container to separate infectious microbes from the water content as it is removed; and
   discarding said storage container, with the infectious microbes from said waste liquid still within the container, together with said filter;
   wherein said filter comprises a secondary filter capable of separating infectious microbes and a primary filter for preventing the blocking of said secondary filter, said primary filter being disposed in surrounding relationship to said secondary filter.
2. The method of treating a waste liquid containing a body fluid according to claim 1, wherein a filter capable of separating bacteria is used as said secondary filter.
3. The method of treating a waste liquid containing a body fluid according to claim 2, wherein the step of filtering includes pressurizing the interior of said storage container or sucking a discharge side of said filter.
4. The method of treating a waste liquid containing a body fluid according to claim 1, wherein a filter capable of separating virus is used as said secondary filter.
5. The method of treating a waste liquid containing a body fluid according to claim 1, wherein the step of filtering includes pressurizing the interior of said storage container or sucking a discharge side of said filter.
6. The method of treating a waste liquid containing a body fluid according to claim 1, wherein at least one of said sucking and removing steps are performed while supporting a bottom end of the storage container on a support means with the discharge tube received therein with clearance.
7. The method of treating a waste liquid containing a body fluid according to claim 6, wherein said supporting is performed by disposing the storage container within a pressure reducing vessel having a reduced diameter cylindrical portion projecting from a bottom end of the vessel, the discharge tube being accommodated within the cylindrical portion with the storage container disposed thereabove.

8. The method of treating a waste liquid-containing a body fluid according to claim 6, wherein said supporting is performed by disposing the storage container on a generally cylindrical base having an upper edge sized for engaging around a substantial portion of a lower peripheral edge of the storage container.

9. The method of treating a waste liquid containing a body fluid according to claim 6, wherein said supporting is performed during said removing step by disposing the storage container on a generally cylindrical base which surrounds an insertion port for the discharge tube on a top end of a tank.

10. A container for treating a waste liquid containing a body liquid comprising:
    a storage container for storing of a waste liquid containing a body fluid, said storage container being made of a synthetic resin and being provided with an inlet and an outlet;
    wherein said storage container includes a microporous filter to separate infectious microbes and a discharge tube for discharging a water content in the waste liquid after passing through said filter, said discharge tube being provided with a valve, and said filter being disposed between an interior space of the container and an inlet end of said discharge tube; and wherein said filter includes a secondary filter capable of separating infectious microbes and a primary filter for preventing the blocking of said secondary filter, said primary filter being disposed in surrounding relationship to said secondary filter.

11. The container for treating a waste liquid containing a body fluid according to claim 10, wherein a filter capable of separating bacteria is used as said secondary filter.

12. The container for treating a waste liquid containing a body fluid according to claim 11, wherein said filter is provided at such a position as to project from an inner surface of said storage container toward an inside thereof.

13. The container for treating a waste liquid containing a body fluid according to claim 10, wherein a filter capable of separating viruses is used as said secondary filter.

14. The container for treating a waste liquid containing a body fluid according to claim 10, wherein said filter is provided at such a position as to project from an inner surface of said storage container toward an inside thereof.

15. The container for treating a waste liquid containing a body fluid according to claim 14, wherein a filter capable of separating bacteria is used as said filter.

16. The container for treating a waste liquid containing a body fluid according to claim 10, wherein said storage container is formed to be expandable and contractible.

17. The container for treating a waste liquid containing a body fluid according to claim 10, wherein said storage container is formed of a made of a synthetic resin flexible sheet in a bag shape.

18. The container for treating a waste liquid containing a body fluid according to claim 10, wherein said discharge tube extends from a bottom side of the storage container; and wherein support means is provided for supporting the storage container with the discharge tube received therein with clearance.

19. The container for treating a waste liquid containing a body fluid according to claim 18, wherein said support means comprises a generally cylindrical base having an upper edge sized for engaging around a substantial portion of a lower peripheral edge of the storage container.

* * * * *